United States Patent
Jang et al.

(10) Patent No.: US 9,796,923 B2
(45) Date of Patent: Oct. 24, 2017

(54) COLOR TUNABLE MULTIFUNCTIONAL NANOPHOSPHOR, SYNTHESIS METHOD THEREOF, AND POLYMER COMPOSITE INCLUDING THE NANOPHOSPHOR

(71) Applicant: Korea Institute of Science and Technology, Seoul (KR)

(72) Inventors: Ho Seong Jang, Seoul (KR); Kyoungja Woo, Seoul (KR); Su Yeon Kim, Yangju-si (KR)

(73) Assignee: Korea Institute of Science and Technology, Seoul (KR)

( * ) Notice: Subject to any disclaimer, the term of this patent is extended or adjusted under 35 U.S.C. 154(b) by 840 days.

(21) Appl. No.: 14/250,769

(22) Filed: Apr. 11, 2014

(65) Prior Publication Data

US 2014/0308213 A1 Oct. 16, 2014

(30) Foreign Application Priority Data

Apr. 12, 2013 (KR) ........................ 10-2013-0040471

(51) Int. Cl.
| | |
|---|---|
| *A61K 9/00* | (2006.01) |
| *C09K 11/77* | (2006.01) |
| *C09K 11/02* | (2006.01) |
| *A61K 49/00* | (2006.01) |
| *A61K 49/18* | (2006.01) |

(52) U.S. Cl.
CPC ...... *C09K 11/7773* (2013.01); *A61K 49/0067* (2013.01); *A61K 49/1827* (2013.01); *C09K 11/025* (2013.01); *C09K 11/7791* (2013.01)

(58) Field of Classification Search
CPC .................................................. C09K 11/7773
See application file for complete search history.

(56) References Cited

PUBLICATIONS

Korean Office Action dated Dec. 29, 2014 in counterpart Application No. KR 10-2013-0040471 (3 pages, in Korean).
Kiliaan, H. S., et al. "Energy Transfer in the Luminescent System Na (Y, Gd) F 4: Ce, Tb." Journal of the Electrochemical Society 134.9 (1987): 2359-2364.
Wang, Feng, et al. "Multicolour PEI/NaGdF4: Ce3+, Ln3+ nanocrystals by single-wavelength excitation." Nanotechnology vol. 18 (2007): 025701. (6 pages).
Wang, Xiaoyong, et al. "Non-blinking semiconductor nanocrystals." Nature vol. 459 (2009): 686-689.
Sotiriou, Georgios A., et al. "Optically stable biocompatible flame-made SiO2-coated Y2O3: Tb3+ nanophosphors for cell imaging." ACS Nano vol. 6 No. 5 (2012): (14 pages).
Boyer, John-Christopher, et al. "Synthesis, characterization, and spectroscopy of NaGdF4: Ce3+, Tb3+/NaYF4 core/shell nanoparticles." Chemistry of materials 19.14 (2007): 3358-3360.
Korean Notice of Allowance dated Mar. 31, 2015 in Korean counterpart Application No. KR 10-2013-0040471 (2 pages, in Korean).

*Primary Examiner* — Paul Dickinson
(74) *Attorney, Agent, or Firm* — NSIP Law

(57) ABSTRACT

A nanophosphor in accordance with one exemplary embodiment of the present disclosure includes a fluoride-based nanoparticle co-doped with $Ce^{3+}$ and one selected from a group consisting of $Tb^{3+}$, $Eu^{3+}$ and a combination thereof. The nanophosphor may be excited by a single wavelength of ultraviolet rays to emit various colors of green, yellow, orange, red and the like, and exhibit high photostability without photoblinking. The nanophosphor may be utilized as a bio imaging contrast agent, a transparent display device, an anti-counterfeit code and the like.

19 Claims, 9 Drawing Sheets
(7 of 9 Drawing Sheet(s) Filed in Color)

FIG. 1 (color)

FIG. 4 (color)

FIG. 5 (color)

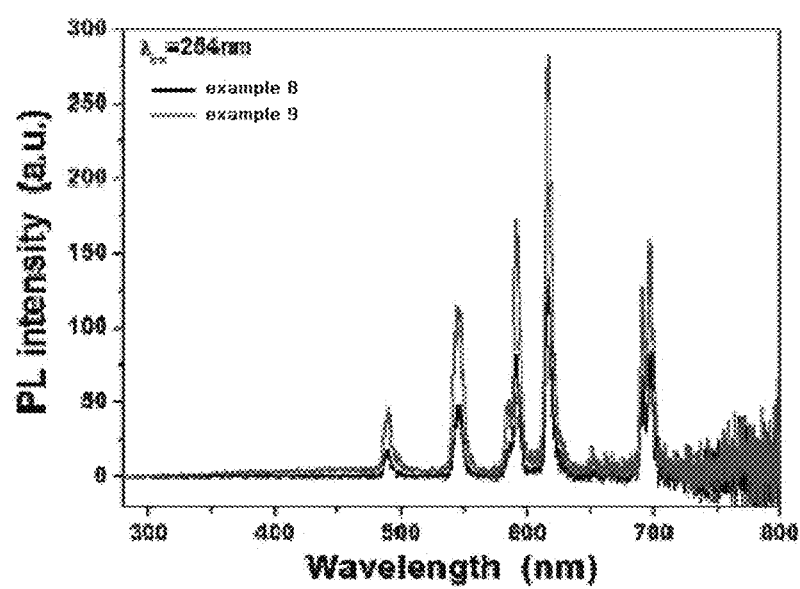
FIG. 8 (color)

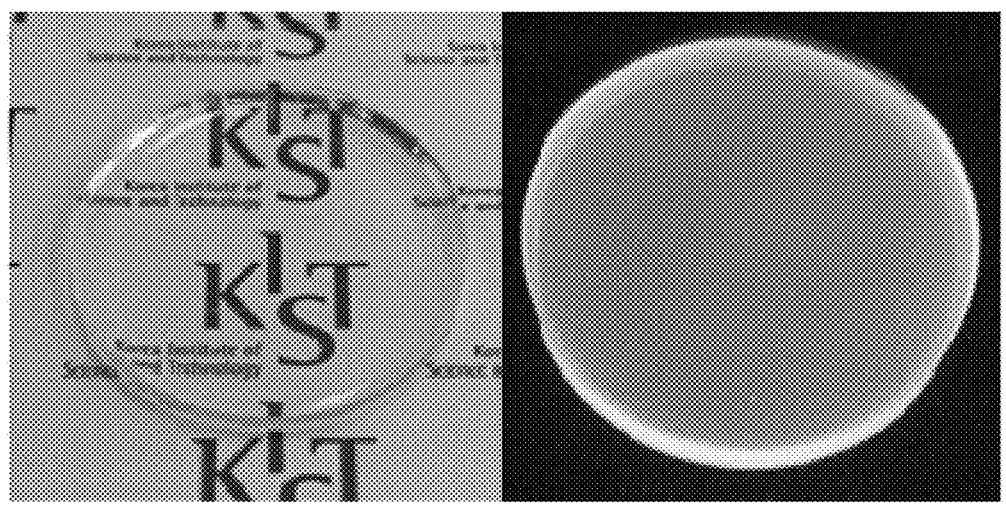
FIG. 9 (color)

COLOR TUNABLE MULTIFUNCTIONAL NANOPHOSPHOR, SYNTHESIS METHOD THEREOF, AND POLYMER COMPOSITE INCLUDING THE NANOPHOSPHOR

CROSS-REFERENCE TO RELATED APPLICATION

Pursuant to 35 U.S.C. §119(a), this application claims the benefit of earlier filing date and right of priority to Korean Application No. 10-2013-0040471, filed on Apr. 12, 2013, the contents of which is incorporated by reference herein in its entirety.

BACKGROUND

1. Field

The following disclosure relates to a color tunable multifunctional nanophosphor, a synthesis method thereof, and a polymer composite including the nanophosphor, and particularly, to a nanophosphor capable of being implemented by tuning various colors of green, yellowish green, yellow, orange, red and the like under a single wavelength excitation in a manner of adjusting doping elements, and a synthesis method thereof. The nanophosphor may also be nanophosphors which are capable of being used as contrast agents of magnetic resonance imaging by forming a shell, and also being applied to transparent displays in a form of polymer composite.

2. Background

Nanophosphors have a structure that lanthanide is doped on an oxide, fluoride, sulfide or nitride-based host material with a size less than 100 nm. A nanophosphor doped with trivalent lanthanide ions except for $Ce^{3+}$ ion represents an inherent luminescent color depending on the doped lanthanide element, irrespective of a type of host [luminescent materials (1994)]. This is because the photoluminescence (luminescence) of the nanophosphor is generated by 4f-4f transition due to 4f electrons of the doped lanthanide 3+ ions. Therefore, a desired photoluminescence wavelength may be advantageously maintained even if sizes of particles are differently adjusted when necessary.

However, since the nanophosphors exhibit fixed luminescent colors, such as red or green, according to doped elements, they have difficulties in obtaining desired luminescent colors, except for several fixed colors. To overcome this problem, upon mixing two or more types of phosphors, which have different luminescent colors, various colors can be implemented but excitation light sources with different wavelengths have to be disadvantageously used. This may result from the fact that each element has a specific absorption wavelength range for photoluminescence via 4f-4f transition, and accordingly the mixed phosphors do not all emit light under a single excitation wavelength.

To solve this problem, Wang, et al. obtained photoluminescence properties of green, red and bluish green colors using a single wavelength around 250 nm in a manner of coating Ce on $NaGdF_4$ particles doped with Tb, Eu, Sm and Dy, respectively, to absorb ultraviolet rays around 250 and transferring the absorbed energy to each lanthanide element [Nanotechnology vol. 18, 025701 (2007)]. However, in this case, only a green-emitting photoluminescence property was obtained when Ce and Tb were co-doped, only a red-emitting photoluminescence property was obtained when Ce and Eu were co-doped, only the red-emitting photoluminescence property was also obtained when Ce and Sm were co-doped, and a bluish-emitting photoluminescence property was obtained when Ce and Dy were co-doped. That is, only an inherent luminescent color emitted by each of Tb, Eu, Sm and Dy was realized. Also, a less amount of the co-doping agent Ce lowers adsorption efficiency of excitation light. This may cause a difficulty in obtaining a strong photoluminescence property.

Also, when using photoluminescence properties of individual nanophosphors, such as bio imaging contrast agents, mixing of various types of nanophosphors for use may not be allowed in some cases. In general, organic to dyes are widely used as the bio imaging contrast agents. The organic dyes have characteristics of representing various luminescent colors and exhibiting high photoluminescence intensity according to types. However, due to extremely low photostability, a slight increase in an exposure time to excitation light may cause drastic lowering of the photoluminescence intensity [ACS Nano vol. 6, 3888-3897 (2012)].

To overcome the problem, attempts are made to apply inorganic luminescent materials, such as quantum dots. However, the quantum dots cause photoblinking of light [Nature vol. 459, 686-689 (2009)], and are difficult to be applied upon containing a heavy metal, such as Cd, for example, containing CdSe.

Therefore, it is seriously necessary to develop a new material which facilitates for luminescent color tuning, and exhibits high photostability without photoblinking. If a nanophosphor which can emit light in various wavelength bands under one excitation wavelength is created, the nanophosphor may be applied as bio imaging contrast agents capable of detecting different materials, and enable the implementation of a display device with ultrahigh image quality, capable of representing various colors.

SUMMARY

Therefore, the present disclosure has been invented to overcome those drawbacks of the related art, and an aspect of the detailed description is to provide a nanophosphor capable of realizing various luminescent colors merely by changing a composition ratio of a doping agent under a single excitation wavelength using Ce, Tb and Eu co-doped on a fluoride-based host material.

The present disclosure relates to a nanophosphor, capable of being applied to contrast agents of magnetic resonance imaging, fluorescent contrast agents and a light emitter of a display device, and a synthesis method thereof, and more particularly, a nanophosphor including fluoride-based nanoparticles, capable of having particle sizes in the range of 1 to 50 nm, emitting visible rays with tunable colors of green, yellowish green, yellow, orange, red and the like by virtue of excitation by ultraviolet rays, and having a β-phase hexagonal structure with a magnetic characteristic, and a synthesis thereof.

To achieve these and other advantages and in accordance with the purpose of this specification, as embodied and broadly described herein, a nanophosphor in accordance with one exemplary embodiment may include a fluoride-based nanoparticle expressed by the following chemical formula 1 and co-doped with $Ce^{3+}$ and one selected from a group consisting of $Tb^{3+}$, $Eu^{3+}$ and any combination thereof.

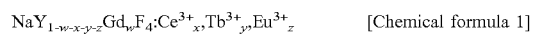

$$NaY_{1-w-x-y-z}Gd_wF_4:Ce^{3+}{}_x,Tb^{3+}{}_y,Eu^{3+}{}_z \qquad \text{[Chemical formula 1]}$$

In Chemical Formula 1, x denotes a real number in the range of $0.1 \le x \le 0.5$, y denotes a real number in the range of $0 \le y \le 0.4$, z denotes a real number in the range of $0 \le z \le 0.3$, and w denotes a real number in the range of $0 \le w \le 0.9$. Also, $0 < y+z$ and $0 \le w+x+y+z \le 1$ are satisfied.

A nanophosphor in accordance with another exemplary embodiment may have a core-shell structure which includes a core expressed by chemical formula 1 and comprising a fluoride-based nanoparticle co-doped with $Ce^{3+}$ and one selected from a group consisting of $Tb^{3+}$, $Eu^{3+}$ and any combination thereof, and a shell covering a surface of the core. The shell may consist of a compound expressed by the following chemical formula 2.

$$NaGd_{1-r}M_rF_4 \qquad \text{[Chemical formula 2]}$$

In Chemical Formula 2, r denotes a real number in the range of $0 \leq r < 1$, and M denotes one selected from a group consisting of yttrium (Y), a lanthanide element and a combination thereof.

A size of the fluoride-based nanoparticle may be in the range of 1 to 50 nm.

The size of the fluoride-based nanoparticle may be below 5 nm.

The fluoride-based nanoparticle may have a hexagonal structure.

The core-shell nanophosphor may be greater than 1 nm and smaller than or equal to 60 nm.

The nanophosphor may have a down-conversion photoluminescence property of emitting a green, yellowish green, yellow, orange or red color under a single wavelength excitation according to the content of the lanthanide element.

The nanophosphor may include a fluoride-based nanoparticle containing $Tb^{3+}$ and $Eu^{3+}$ in a molar ratio of 30 to 15:1, and have a yellowish green-emitting photoluminescence property.

The nanophosphor may include a fluoride-based nanoparticle containing $Tb^{3+}$ and $Eu^{3+}$ in a molar ratio of 7 to 8:1, and have a yellow-emitting photoluminescence property.

The nanophosphor may include a fluoride-based nanoparticle containing $Tb^{3+}$ and $Eu^{3+}$ in a molar ratio of 3 to 4:1, and have an orange-emitting photoluminescence property.

The nanophosphor may include a fluoride-based nanoparticle containing to $Tb^{3+}$ and $Eu^{3+}$ in a molar ratio of 1 to 2:1, and have a scarlet-emitting photoluminescence property.

A method of synthesizing a nanophosphor in accordance with another exemplary embodiment may comprise a complex compound preparing step of preparing a lanthanide complex compound by heat treatment for a mixture containing at least one selected from a group, which consists of terbium precursor and europium precursor, yttrium precursor, gadolinium precursor, cerium precursor, oleic acid, and a mixture solvent, a first mixed-solution preparing step of mixing the lanthanide complex compound with a solution containing oleic acid and 1-octadecene to prepare a first mixed-solution containing the lanthanide complex compound, a reaction-solution preparing step of mixing the first mixed-solution with a second mixed-solution containing sodium precursor, fluorine precursor and alcohol to prepare a reaction-solution, and a nanoparticle preparing step of forming a fluoride-based nanoparticle by removing the alcohol from the reaction-solution, followed by heat treatment. The fluoride-based nanoparticle may be expressed by the chemical formula 1.

The yttrium precursor may be one selected from a group consisting of yttrium acetate ($Y(CH_3COO)_3$), yttrium chloride ($YCl_3$), yttrium chloride hydrate ($YCl_3 \cdot 6H_2O$), and any combination thereof.

The gadolinium precursor may be one selected from a group consisting of gadolinium acetate ($Gd(CH_3COO)_3$), gadolinium chloride ($GdCl_3$), gadolinium chloride hydrate ($GdCl_3 \cdot 6H_2O$), and any combination thereof.

The cerium precursor may be one selected from a group consisting of cerium acetate ($Ce(CH_3COO)_3$), cerium chloride ($CeCl_3$), cerium chloride hydrate ($CeCl_3 \cdot 7H_2O$), and any combination thereof.

The terbium precursor may be one selected from a group consisting of terbium acetate ($Tb(CH_3COO)_3$), terbium chloride ($TbCl_3$), terbium chloride hydrate ($TbCl_3 \cdot 6H_2O$), and any combination thereof.

The europium precursor may be one selected from a group consisting of europium acetate ($Eu(CH_3COO)_3$), europium chloride ($EuCl_3$), europium chloride hydrate ($EuCl_3 \cdot 6H_2O$), and any combination thereof.

The heat treatment in the nanoparticle preparing step may be carried out at temperature of 200° C. to 370° C. for 10 minutes to four hours.

The synthesis method may further include a shell preparing step after the nanoparticle preparing step.

The shell preparing step may include a shell solution preparing step of preparing a third mixed-solution containing lanthanide precursor, which includes gadolinium precursor, oleic acid, and 1-octadecene, a nanoparticle mixing step of heat-treating the third mixed-solution to form gadolinium oleate therein and mixing the heat-treated third mixed-solution with fluoride-based nanoparticles to prepare a fourth mixed-solution, a shell reaction-solution preparing step of mixing the fourth mixed-solution with a solution containing sodium precursor, fluorine precursor and alcohol to prepare a shell reaction-solution, and a shell forming step of growing a shell on a surface of a core, which comprises the fluoride-based nanoparticles, by removing the alcohol from the shell reaction-solution, followed by heat treatment. The shell may consist of a compound expressed by the chemical formula 2.

The gadolinium precursor may be one selected from a group consisting of gadolinium acetate ($Gd(CH_3COO)_3$), gadolinium chloride ($GdCl_3$), gadolinium chloride hydrate ($GdCl_3 \cdot 6H_2O$), and any combination thereof.

A nanophosphor-polymer composite in accordance with another exemplary embodiment may include the nanophosphor and polymer.

A contrast agent in accordance with another exemplary embodiment may include the nanophosphor, and may be a fluorescent contrast agent or contrast agent of magnetic resonance imaging.

An anti-counterfeit code in accordance with another exemplary embodiment may include the nanophosphor.

Hereinafter, the present disclosure will be described in more detail.

A nanophosphor in accordance with the present disclosure may include a fluoride-based nanoparticle co-doped with $Ce^{3+}$ and one selected from a group consisting of $Tb^{3+}$, $Eu^{3+}$ and a combination thereof. The fluoride-based nanoparticle may be expressed by the following Chemical Formula 1.

$$NaY_{1-w-x-y-z}Gd_wF_4:Ce^{3+}_x,Tb^{3+}_y,Eu^{3+}_z \qquad \text{[Chemical formula 1]}$$

In Chemical Formula 1, x denotes a real number in the range of $0.1 \leq x \leq 0.5$, y denotes a real number in the range of $0 \leq y \leq 0.4$, z denotes a real number in the range of $0 \leq z \leq 0.3$, w denotes a real number in the range of $0 \leq w \leq 0.9$. Also, $0 < y+z$ and $0 \leq w+x+y+z \leq 1$ are satisfied.

The y may be a real number in the range of $0 < y \leq 0.4$ and the z may be a real number in the range of $0 < z \leq 0.3$. A molar ratio of y and z may be 1:0.03 to 0.7.

The fluoride-based nanoparticle may provide the nanophosphor, which is capable of emitting light of various colors from green to red by virtue of the co-doped $Ce^{3+}$ and $Tb^{3+}$ and/or $Eu^{3+}$. In detail, $Ce^{3+}$ as the co-dopant of the nanophosphor may absorb light, and transfer the absorbed energy to $Tb^{3+}$ and/or $Eu^{3+}$, thereby exhibiting photoluminescence peak in a green and red region and acquiring a desired luminescent color by adjusting a relative quantity thereof.

For example, upon being co-doped with only $Ce^{3+}$ and $Eu^{3+}$ (i.e., without $Tb^{3+}$), a red luminescent color may be emitted. On the contrary, upon being co-doped with only $Ce^{3+}$ and $Tb^{3+}$ (i.e., without $Eu^{3+}$), a bluish green luminescent color may be emitted. Also, a yellowish green luminescent color may be emitted when $Tb^{3+}$ and $Eu^{3+}$ are contained in a molar ratio of 30 to 15:1, a yellow luminescent color may be emitted when $Tb^{3+}$ and $Eu^{3+}$ are contained in a molar ratio of 7 to 8:1, an orange luminescent color may be emitted when $Tb^{3+}$ and $Eu^{3+}$ are contained in a molar ratio of 3 to 4:1, and a scarlet luminescent color may be emitted when $Tb^{3+}$ and $Eu^{3+}$ are contained in a molar ratio of 1 to 2:1.

By use of such photoluminescence by electron transition of the lanthanide elements, nanophosphors, which exhibits high photostability without photoblinking, and have various luminescent colors from green to yellow and red by adjusting contents of elements co-doped.

The fluoride-based nanoparticle may have a size in the range of 1 to 50 nm, or in the range of 1 to 10 nm. Especially, when a size of the fluoride-based nanoparticle is 10 nm or less, it may result in sufficient reduction of the size of the nanophosphor, so as to be applied to in vivo imaging. Also, the fluoride-based nanoparticle comprised in the nanophosphor may have a size less than 5 nm. By virtue of the sufficiently fine fluoride-based nanoparticles, the nanophosphors with the size small enough to be appropriate for in vivo imaging even when forming the shell later may be provided.

The nanoparticle may have a hexagonal structure. The nanophosphor may have a down-conversion property allowing color coordinate tuning.

A nanophosphor according to another exemplary embodiment may be a nanophosphor having a core-shell structure, including a core comprising the fluoride-based nanoparticle and a shell covering a surface of the core. The shell may consist of a compound expressed by the following chemical formula 2.

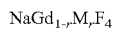
$NaGd_{1-r}M_rF_4$            [Chemical formula 2]

In Chemical Formula 2, r denotes a real number in the range of $0 \leq r < 1$, and M denotes one selected from a group consisting of yttrium (Y), lanthanide element and a combination thereof.

The lanthanide element may be one selected from a group consisting of La, Pr, Nd, Pm, Sm, Er, Gd, Dy, Ho, Tm and Lu.

The shell may be crystalline and formed by epitaxial growth. When the shell is epitaxially grown into a crystalline shell, a surface defect of the nanoparticle may be reduced, which may result in obtaining high photoluminescence properties.

The size of the nanophosphor having the core-shell structure may be 60 nm or less, greater than 2 nm and 60 nm or less, or 10 nm or less.

The nanophosphor, which comprises the fluoride-based nanoparticle, as the core, co-doped with $Ce^{3+}$, $Tb^{3+}$ and/or $Eu^{3+}$ having high luminescence intensities, may exhibit superior photoluminescence properties even with such fine size. This may allow the nanophosphors to be applied to in vitro experiment and in vivo experiment.

The nanophosphor may include the core expressed by Chemical Formula 1 and the shell expressed by Chemical Formula 2, so as to implement high luminescence intensity in spite of the fine size.

A method of synthesizing a nanophosphor in accordance with another exemplary embodiment may include a complex compound preparing step, a first mixed-solution preparing step, a reaction-solution preparing step, and a nanoparticle preparing step. The nanoparticle may be a fluoride-based nanoparticle, co-doped with $Ce^{3+}$ and one selected from a group consisting of $Tb^{3+}$, $Eu^{3+}$, and a combination thereof.

The complex compound preparing step may include a process of preparing a lanthanide complex compound by heat-treating a mixture, which contains at least one selected from a group consisting of terbium precursor and europium precursor, yttrium precursor, gadolinium precursor, a cerium precursor, oleic acid and a mixture solvent.

The terbium precursor may be one selected from a group consisting of terbium acetate ($Tb(CH_3COO)_3$), terbium chloride ($TbCl_3$), terbium chloride hydrate ($TbCl_3.6H_2O$), and any combination thereof. The europium precursor may be one selected from a group consisting of europium acetate ($Eu(CH_3COO)_3$), europium chloride ($EuCl_3$), europium chloride hydrate ($EuCl_3.6H_2O$), and any combination thereof. The yttrium precursor may be one selected from a group consisting of yttrium acetate ($Y(CH_3COO)_3$), yttrium chloride ($YCl_3$), yttrium chloride hydrate ($YCl_3.6H_2O$), and any combination thereof. The gadolinium precursor may be one selected from a group consisting of gadolinium acetate ($Gd(CH_3COO)_3$), gadolinium chloride ($GdCl_3$), gadolinium chloride hydrate ($GdCl_3.6H_2O$), and any combination thereof. The cerium precursor may be one selected from a group consisting of cerium acetate ($Ce(CH_3COO)_3$), cerium chloride ($CeCl_3$), cerium chloride hydrate ($CeCl_3.7H_2O$), and any combination thereof.

The oleate may be one selected from a group consisting of sodium oleate ($C_{18}H_{33}O_2Na$), potassium oleate ($C_{18}H_{33}O_2K$), and any combination thereof.

The mixture solvent may be applied if it can dissolve the precursors, the oleic acid and the like, preferably, a mixed solution of water, alcohol and hexane may be applied as the mixture solvent.

The heat treatment of the complex compound preparing step may be carried out at temperature in the range of 40 to 90° C., or in the range of 60 to 80° C. When heating of the mixture is carried out within the temperature range, the lanthanide oleate complex compound may be well formed.

The first mixed-solution preparing step may include a process of preparing a first mixed-solution containing the lanthanide complex compound by mixing the lanthanide complex compound with a solution which contains oleic acid and 1-octadecene. After the mixing, heat treatment may further be carried out so as to prepare the first mixed-solution containing the lanthanide complex compound. The heat treatment of the first mixed-solution preparing step may be carried out at temperature in the range of 100 to 200° C., or in the range of 130 to 180° C. When the heat treatment of the first mixed-solution preparing step is carried out within the temperature range, a mixed solution in which the lanthanide complex compound is uniformly dispersed may be prepared.

The reaction-solution preparing step may include a process of preparing a reaction-solution by mixing the first mixed-solution with a second mixed-solution containing sodium precursor, fluorine precursor and alcohol.

The sodium precursor may be one selected from a group consisting of sodium hydroxide, sodium fluoride, and a combination thereof. The fluorine precursor may be one selected from a group consisting of ammonium fluoride, sodium fluoride, and a combination thereof. The sodium fluoride may be applied as not only the sodium precursor but also the fluorine precursor.

The nanoparticle preparing step may include a process of preparing fluoride-based nanoparticles by removing alcohol from the reaction-solution and heat-treating the alcohol-removed reaction-solution.

The heat treatment may be carried out at temperature of 200 to 370° C. for 20 minutes to 4 hours, or at temperature of 250 to 330° C. for 50 minutes to 3 hours, under an inert gas atmosphere.

When the heat treatment is carried out within the temperature ranges and the time ranges, β-phase nano-crystalline particles having high crystalline properties may be formed. Accordingly, the nanophosphors may exhibit high photoluminescence properties. When the heat treatment temperature below 200° C., a single β-phase nanocrystal may be formed incompletely and low luminescence intensity may be exhibited. When the heat treatment temperature exceeds 370° C., particle lumping may be caused, nanoparticles may not be evenly dispersed in a solution, and brightness of the nanoparticles may be lowered.

The method may further include a shell preparing step after the nanoparticle preparing step. The shell preparing step may include a shell solution preparing step, a nanoparticle mixing step, a shell reaction-solution preparing step, and a shell preparing step.

The shell solution preparing step may include a process of preparing a third mixed-solution containing oleic acid, 1-octadecene, and lanthanide precursor including gadolinium precursor. The gadolinium precursor may be one selected from a group consisting of gadolinium acetate (Gd($CH_3COO)_3$), gadolinium chloride ($GdCl_3$), gadolinium chloride hydrate ($GdCl_3.6H_2O$), and any combination thereof.

The nanoparticle mixing step may include a process of preparing a fourth mixed-solution by mixing the third mixed-solution with the nanoparticles formed in the nanoparticle preparing step.

The nanoparticle formed in the nanoparticle preparing step may be a nanoparticle formed in the nanoparticle preparing step or a nanoparticle which has been cooled or washed.

The shell reaction-solution preparing step may include a process of preparing a shell reaction-solution by mixing the fourth mixed-solution with a solution containing sodium precursor, fluorine precursor and alcohol.

The sodium precursor may be one selected from a group consisting of sodium hydroxide, sodium fluoride, and a combination thereof. The fluorine precursor may be one selected from a group consisting of ammonium fluoride, sodium fluoride, and a combination thereof. The sodium fluoride may be applied as not only the sodium precursor but also the fluorine precursor.

The shell forming step may include a process of growing the shell on a surface of a core comprising the nanoparticles, by removing the alcohol from the shell reaction-solution and heat-treating the alcohol-removed shell reaction-solution.

The heat treatment may be carried out at temperature of 200 to 370° C. for 20 minutes to 4 hours, or at temperature of 250 to 330° C. for 50 minutes to 3 hours, under an inert gas atmosphere.

When the heat treatment is carried out within the temperature ranges and the time ranges, a β-phase nanocrystalline shell may be epitaxially formed, and the nanophosphor may exhibit photoluminescence properties, which is more excellent than that of a nanophosphor formed merely including the nanoparticles, in spite of its fine size.

When the heat treatment temperature is less than 200° C., a single β-phase crystalline shell may be incompletely formed. When the heat treatment temperature is greater than 370° C., the shell precursor may form even the core as well as the shell. This may interfere with effective formation of the shell.

The fluoride-based nanoparticle or nanophosphor fabricated through those processes may be stored by being dispersed in a non-polar solvent. The non-polar solvent may be one selected from a group consisting of hexane, toluene, chloroform, and any combination thereof, but may not be limited to this.

The nanophosphor according to the present disclosure may exhibit high luminescence intensity and realize various luminescent colors, by way of doping onto one host at least one of a lanthanide element emitting a green color and a lanthanide element emitting a red color and doping onto the host a co-doping agent which can effectively adsorb excitation energy to transfer to the doping agent.

A nanophosphor-polymer composite according to another exemplary embodiment may include the nanophosphor and polymer. The polymer may be implemented by any one if it can adsorb the excitation energy of the nanophosphor and does not interfere with photoluminescence of the nanophosphor. Preferably, the polymer may be one selected from a group consisting of polydimethylsiloxane, polymethylmethacrylate, and a combination thereof. The nanophosphor may be a nanophosphor comprising the fluoride-based nanoparticles or a nanophosphor having a core-shell structure, which further includes the shell on a surface of the core comprising the nanoparticle.

The nanophosphor-polymer composite may be prepared by mixing the nanophosphor, polymer or monomer thereof, and an additive (curing agent, etc.). The nanophosphor-polymer composite may also be molded into a shape of film and the like. Specifically, when the nanophosphor is prepared into a composite by being synthesized with a transparent polymer, the composite may exhibit high transparency and excellent photoluminescence property, and a flexible composite may also be synthesized according to a type of polymer. The composite may be applied as an element of a transparent display device.

A contrast agent in accordance with another exemplary embodiment may include the nanophosphor. The contrast agent may be a fluorescent contrast agent or a contrast agent for magnetic resonance imaging. The nanophosphor may be a nanophosphor comprising the fluoride-based nanoparticle or a nanophosphor having the core-shell structure further including the shell on a surface of the core comprising the nanoparticle.

An anti-counterfeit code in accordance with another exemplary embodiment may include the nanophosphor. The nanophosphor may be a nanophosphor comprising the fluoride-based nanoparticle or a nanophosphor having the core-shell structure further including the shell on a surface of the core comprising the nanoparticle. The anti-counterfeit code may be implemented by generating patterns each with a predetermined shape using nanoparticles emitting different luminescent colors and applying each of the patterns as a security code. The security codes may also be distinguishable by various luminescent colors emitted by a single wavelength excitation, as well as the shapes of patterns. This may allow for applying the anti-counterfeit code with high reliability.

Nanophosphors according to the present disclosure may emit various luminescent colors of green, yellow, orange, red and the like by being excited by ultraviolet rays of single wavelength, and exhibit photostability without photoblinking. The nanophosphors may be utilizable as bio imaging contrast agents capable of detecting various materials, and applicable to transparent display devices. Also, upon generating patterns with predetermined shapes using nanoparticles of different compositions emitting different luminescent colors, the patterns may be applicable as security codes, allowing for utilization in various fields.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are included to provide a further understanding of the disclosure and are incorporated in and constitute a part of this specification, illustrate exemplary embodiments and together with the description serve to explain the principles of the disclosure.

In the drawings:

FIG. 1 illustrates photoluminescence (PL) spectra of respective Examples with varied contents of Tb and Eu of Na(Y,Gd)$F_4$:Ce,Tb,Eu nanophosphor in accordance with an exemplary embodiment of the present disclosure;

FIG. 2 illustrates TEM images of respective Examples with varied contents of Tb and Eu of Na(Y,Gd)$F_4$:Ce,Tb,Eu nanophosphor in accordance with an exemplary embodiment of the present disclosure;

FIG. 3 illustrates X-ray diffraction patterns of respective Examples with varied contents of Tb and Eu of Na(Y,Gd)$F_4$:Ce,Tb,Eu nanophosphor in accordance with an exemplary embodiments of the present disclosure;

FIG. 4 illustrates color coordinates of luminescent colors of each Example with varied contents of Tb and Eu of Na(Y,Gd)$F_4$:Ce,Tb,Eu nanophosphor in accordance with an exemplary embodiment of the present disclosure;

FIG. 5 illustrates luminescence images of nanophosphor solutions of each Example with varied contents of Tb and Eu of Na(Y,Gd)$F_4$:Ce,Tb,Eu nanophosphor in accordance with an exemplary embodiment of the present disclosure;

FIG. 6 is a TEM image of Na(Y,Gd)$F_4$:Ce,Tb,Eu core nanophosphor having a size less than 10 nm in accordance with an exemplary embodiments of the present disclosure;

FIG. 7 is a TEM image of Na(Y,Gd)$F_4$:Ce,Tb,Eu/NaGd$F_4$ core-shell nanophosphor in accordance with an exemplary embodiment of the present disclosure;

FIG. 8 illustrates a PL spectrum of Na(Y,Gd)$F_4$:Ce,Tb,Eu/NaGd$F_4$ core-shell nanophosphor in accordance with an exemplary embodiment of the present disclosure; and FIG. 9 is an image of a polymer composite that Na(Y,Gd)$F_4$:Ce,Tb,Eu/NaGd$F_4$ core-shell nanophosphor is dispersed in polydimethylsiloxane (PDMS) polymer in accordance with an exemplary embodiment of the present disclosure.

DETAILED DESCRIPTION

Figure 1:
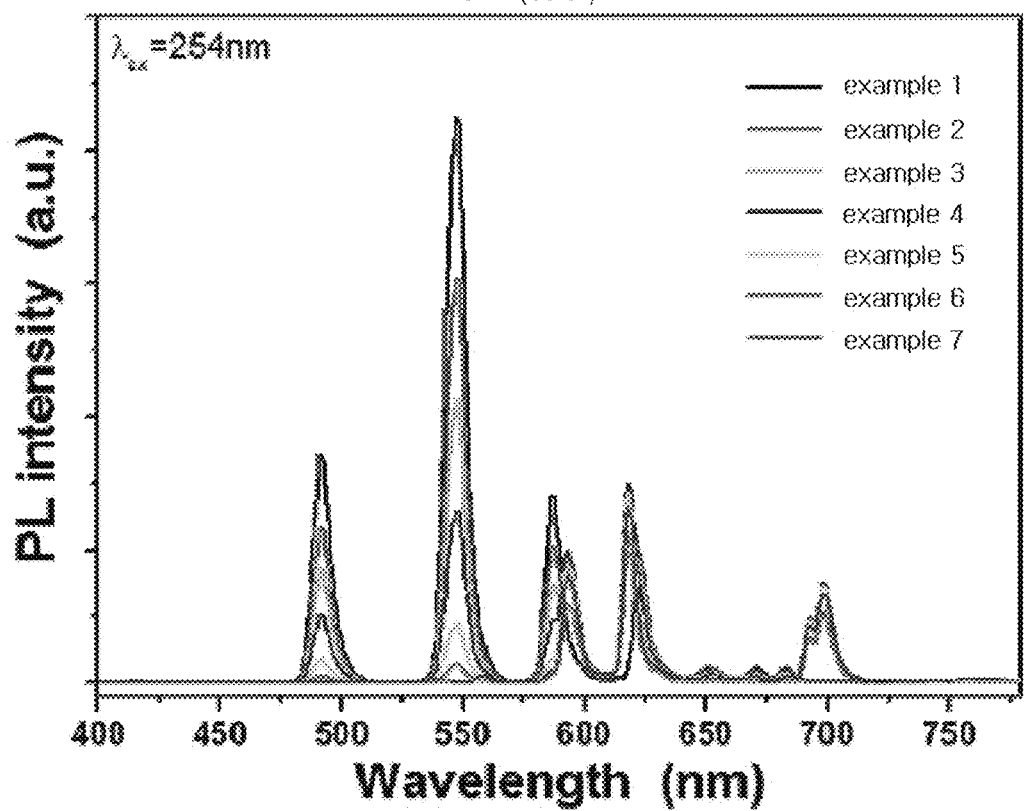

Description will now be given in detail of the exemplary embodiments, with reference to the accompanying drawings, to be easily practiced by a person skilled in the art to which the present disclosure belongs. However, the present disclosure may be implemented in various forms, without being limited to the exemplary embodiments disclosed herein.

Example 1: Synthesis of Green-Emitting Nanophosphor as 0.1 mmol $Ce^{3+}$, 0.15 mmol $Tb^{3+}$, and 0 mmol $Eu^{3+}$-Doped Fluoride-Based Nanoparticle 0.15 mmol of yttrium chloride hydrate ($YCl_3.6H_2O$), 0.6 mmol of gadolinium chloride hydrate ($GdCl_3.6H_2O$), 0.1 mmol of cerium chloride hydrate ($CeCl_3.7H_2O$), 0.15 mmol of terbium chloride hydrate ($TbCl_3.6H_2O$), and 3.1 mmol of sodium oleate ($C_{18}H_{33}NaO_2$) were weighed, respectively, to be added into a mixture solvent (with a mixture of water, ethanol, and hexane), thereby preparing a mixture. The mixture was heat treated at 70° C. to prepare a lanthanide complex compound (Complex compound preparing step).

The lanthanide complex compound was mixed with a solution containing oleic acid and 1-octadicene, and heat-treated at 150° C. for 30 minutes, preparing a first mixed-solution containing the lanthanide complex compound (First mixed-solution preparing step).

2.5 mmol of sodium hydroxide was mixed with 10 ml of methanol solution containing 4 mmol of ammonium fluoride, to prepare a second mixed-solution. The second mixed-solution was then mixed with the first mixed-solution, to prepare a reaction-solution (Reaction-solution preparing step).

After fully mixing the reaction-solution, the methanol was removed, followed by heat treatment under an inert gas atmosphere. The heat treatment was carried out at 320° C. for 1.5 hours (Nanoparticle preparing step).

After completion of the heat treatment of the nanoparticle preparing step, the reaction-solution was cooled down to room temperature, thereby obtaining a nanophosphor of Example 1 which was in a colloid state having a diameter of about 18.5 nm. The thusly obtained nanophosphor of Example 1 was washed with acetone or ethanol, and stored by being dispersed in a non-polar solvent, such as hexane, toluene, chloroform and the like.

Example 2: Fabrication of Yellowish Green-Emitting Nanophosphor as 0.1 mmol $Ce^{3+}$, 0.15 mmol $Tb^{3+}$, and 0.005 mmol $Eu^{3+}$-Doped Fluoride-Based Nanoparticle A reaction-solution was prepared by carrying out the complex compound preparing step, the first mixed-solution preparing step and the reaction-solution preparing step, as equal to Example 1, except for a mixture, applied in the complex compound preparing step, which was prepared by adding in a mixture solvent 0.145 mmol of yttrium chloride hydrate ($YCl_3.6H_2O$), 0.6 mmol of gadolinium chloride hydrate ($GdCl_3.6H_2O$), 0.1 mmol of cerium chloride hydrate ($CeCl_3.7H_2O$), 0.15 mmol of terbium chloride hydrate (TbCl$_3$.6H$_2$O), 0.005 mmol of europium chloride hydrate (EuCl$_3$.6H$_2$O), and 3.1 mmol of sodium oleate (C$_{18}$H$_{33}$NaO$_2$).

Afterwards, the heat treatment of the nanoparticle preparing step was carried out at 320° C. for 1.5 hours. After completion of the heat treatment, the reaction-solution was cooled down to room temperature, thereby obtaining a nanophosphor of Example 2 which was in a colloid state having a diameter of about 16.5 nm. The thusly obtained nanophosphor of Example 2 was stored as equal to Example 1.

Example 3: Fabrication of Greenish Yellow-Emitting Nanophosphor as 0.1 mmol Ce$^{3+}$, 0.15 mmol Tb$^{3+}$, and 0.01 mmol Eu$^{3+}$-Doped Fluoride-Based Nanoparticle A reaction-solution was prepared by carrying out the complex compound preparing step, the first mixed-solution preparing step and the reaction-solution preparing step, as equal to Example 1, except for a mixture, applied in the complex compound preparing step, which was prepared by adding in a mixture solvent 0.14 mmol of yttrium chloride hydrate (YCl$_3$.6H$_2$O), 0.6 mmol of gadolinium chloride hydrate (GdCl$_3$.6H$_2$O), 0.1 mmol of cerium chloride hydrate (CeCl$_3$.7H$_2$O), 0.15 mmol of terbium chloride hydrate (TbCl$_3$.6H$_2$O), 0.01 mmol of europium chloride hydrate (EuCl$_3$.6H$_2$O), and 3.1 mmol of sodium oleate (C$_{18}$H$_{33}$NaO$_2$).

Afterwards, the heat treatment of the nanoparticle preparing step was carried out at 320° C. for 1.5 hours. After completion of the heat treatment, the reaction-solution was cooled down to room temperature, thereby obtaining a nanophosphor of Example 3 which was in a colloid state having a diameter of about 15.7 nm. The thusly obtained nanophosphor of Example 3 was stored as equal to Example 1.

Example 4: Fabrication of Yellow-Emitting Nanophosphor as 0.1 mmol Ce$^{3+}$, 0.15 mmol Tb$^{3+}$, and 0.02 mmol Eu$^{3+}$-Doped Fluoride-Based Nanoparticle A reaction-solution was prepared by carrying out the complex compound preparing step, the first mixed-solution preparing step and the reaction-solution preparing step, as equal to Example 1, except for a mixture, applied in the complex compound preparing step, which was prepared by adding in a mixture solvent 0.13 mmol of yttrium chloride hydrate (YCl$_3$.6H$_2$O), 0.6 mmol of gadolinium chloride hydrate (GdCl$_3$.6H$_2$O), 0.1 mmol of cerium chloride hydrate (CeCl$_3$.7H$_2$O), 0.15 mmol of terbium chloride hydrate (TbCl$_3$.6H$_2$O), 0.02 mmol of europium chloride hydrate (EuCl$_3$.6H$_2$O), and 3.1 mmol of sodium oleate (C$_{18}$H$_{33}$NaO$_2$).

Afterwards, the heat treatment of the nanoparticle preparing step was carried out at 320° C. for 1.5 hours. After completion of the heat treatment, the reaction-solution was cooled down to room temperature, thereby obtaining a nanophosphor of Example 4 which was in a colloid state having a diameter of about 15.5 nm. The thusly obtained nanophosphor of Example 4 was stored as equal to Example 1.

Example 5: Fabrication of Orange-Emitting Nanophosphor as 0.1 mmol Ce$^{3+}$, 0.15 mmol Tb$^{3+}$, and 0.05 mmol Eu$^{3+}$-Doped Fluoride-Based Nanoparticle A reaction-solution was prepared by carrying out the complex compound preparing step, the first mixed-solution preparing step and the reaction-solution preparing step, as equal to Example 1, except for a mixture, applied in the complex compound preparing step, which was prepared by adding in a mixture solvent 0.1 mmol of yttrium chloride hydrate (YCl$_3$.6H$_2$O), 0.6 mmol of gadolinium chloride hydrate (GdCl$_3$.6H$_2$O), 0.1 mmol of cerium chloride hydrate (CeCl$_3$.7H$_2$O), 0.15 mmol of terbium chloride hydrate (TbCl$_3$.6H$_2$O), 0.05 mmol of europium chloride hydrate (EuCl$_3$.6H$_2$O), and 3.1 mmol of sodium oleate (C$_{18}$H$_{33}$NaO$_2$).

Afterwards, the heat treatment of the nanoparticle preparing step was carried out at 320° C. for 1.5 hours. After completion of the heat treatment, the reaction-solution was cooled down to room temperature, thereby obtaining a nanophosphor of Example 5 which was in a colloid state having a diameter of about 14.6 nm. The thusly obtained nanophosphor of Example 5 was stored as equal to Example 1.

Example 6: Fabrication of Scarlet-Emitting Nanophosphor as 0.1 mmol Ce$^{3+}$, 0.15 mmol Tb$^{3+}$, and 0.1 mmol Eu$^{3+}$-Doped Fluoride-Based Nanoparticle A reaction-solution was prepared by carrying out the complex compound preparing step, the first mixed-solution preparing step and the reaction-solution preparing step, as equal to Example 1, except for a mixture, applied in the complex compound preparing step, which was prepared by adding in a mixture solvent 0.05 mmol of yttrium chloride hydrate (YCl$_3$.6H$_2$O), 0.6 mmol of gadolinium chloride hydrate (GdCl$_3$.6H$_2$O), 0.1 mmol of cerium chloride hydrate (CeCl$_3$.7H$_2$O), 0.15 mmol of terbium chloride hydrate (TbCl$_3$.6H$_2$O), 0.1 mmol of europium chloride hydrate (EuCl$_3$.6H$_2$O), and 3.1 mmol of sodium oleate (C$_{18}$H$_{33}$NaO$_2$).

Afterwards, the heat treatment of the nanoparticle preparing step was carried out at 320° C. for 1.5 hours. After completion of the heat treatment, the reaction-solution was cooled down to room temperature, thereby obtaining a nanophosphor of Example 6 which was in a colloid state having a diameter of about 13.7 nm. The thusly obtained nanophosphor of Example 6 was stored as equal to Example 1.

Example 7: Fabrication of Red-Emitting Nanophosphor as 0.1 mmol Ce$^{3+}$, 0 mmol Tb$^{3+}$, and 0.05 mmol Eu$^{3+}$-Doped Fluoride-Based Nanoparticle A reaction-solution was prepared by carrying out the complex compound preparing step, the first mixed-solution preparing step and the reaction-solution preparing step, as equal to Example 1, except for a mixture, applied in the complex compound preparing step, which was prepared by adding in a mixture solvent 0.25 mmol of yttrium chloride hydrate (YCl$_3$.6H$_2$O), 0.6 mmol of gadolinium chloride hydrate (GdCl$_3$.6H$_2$O), 0.1 mmol of cerium chloride hydrate (CeCl$_3$.7H$_2$O), 0.05 mmol of europium chloride hydrate (EuCl$_3$.6H$_2$O), and 3.1 mmol of sodium oleate (C$_{18}$H$_{33}$NaO$_2$).

Afterwards, the heat treatment of the nanoparticle preparing step was carried out at 320° C. for 1.5 hours. After completion of the heat treatment, the reaction-solution was cooled down to room temperature, thereby obtaining a nanophosphor of Example 7 which was in a colloid state having a diameter of about 16.4 nm. The thusly obtained nanophosphor of Example 7 was stored as equal to Example 1.

Experimental Example: Evaluation of Characteristics of Nanophosphors of Examples 1 to 7

1. Measurement of PL Spectrum

Photoluminescence spectra of the nanophosphors of Examples 1 to 7 have been measured using F-7000 model of Hitachi, and the measurement results are shown in FIG. 1. Referring to FIG. 1, it can be understood that relative intensities of PL peaks from green to red regions are changed in response to variation of the content of europium when the nanophosphor is excited by 254-nm ultraviolet rays. That is, it can be noticed that the green-emitting peak is reduced and the red-emitting peak is increasing as the content of europium increases within the nanoparticle host. It may thusly be observed from such results that the nanophosphors with the tuned PL peaks from green to red regions by adjustment of the content of europium can be fabricated.

2. Observation of TEM Images

Figure 2:
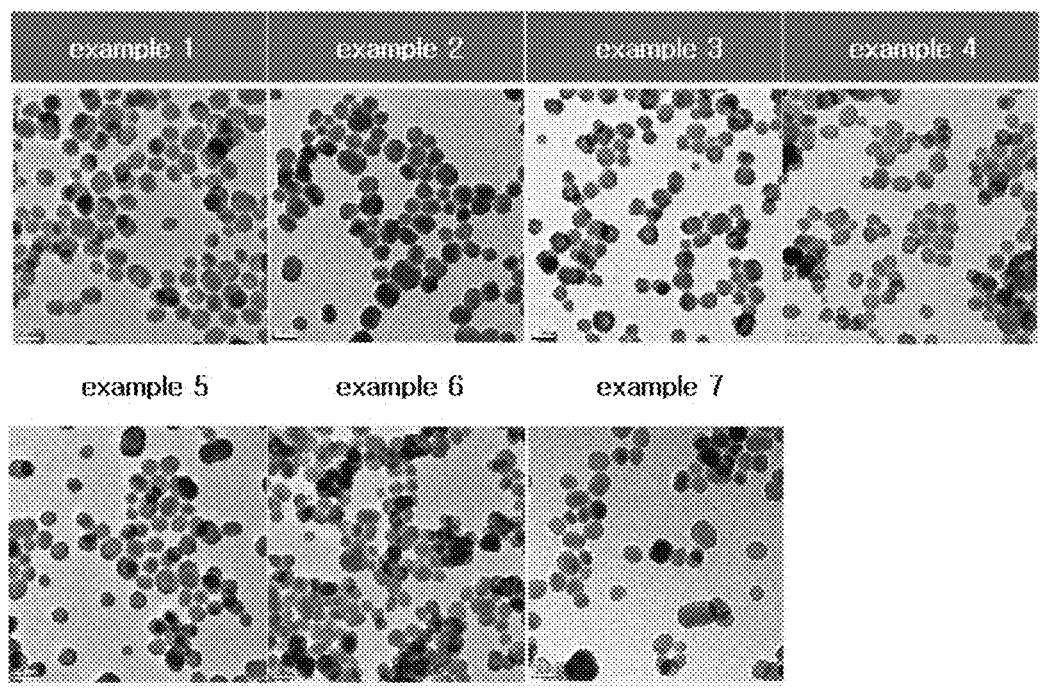

TEM images of the nanophosphors synthesized in Examples 1 to 7 have been measured, respectively, by using FEI TECNAI F20 G2, and the measurement results are shown in FIG. 2. Referring to FIG. 2, it can be observed that the nanophosphors synthesized according to the present disclosure all exhibit nano-scaled sizes less than 50 nm, and have sizes in the range of 13.7 nm to 18.5 nm irrespective of the contents of the doped terbium and europium.

3. Observation of X-ray Diffraction Pattern

Figure 3:
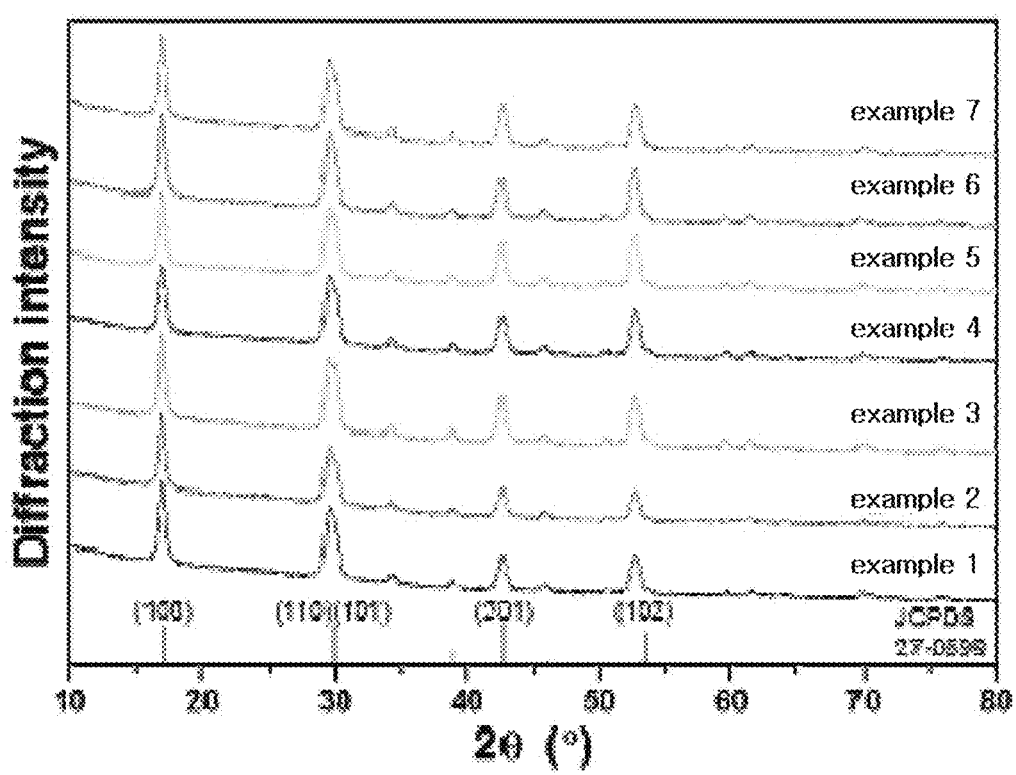

X-ray diffraction patterns of the nanophosphors synthesized in Examples 1 to 7 are shown in FIG. 3. Referring to FIG. 3, it can be observed that a single β-phase without impurities has been formed irrespective of the content of terbium or europium doped. It can also be checked that a full width at half maximum (FWHM) of a diffraction peak has increased upon comparing with a reference x-ray diffraction pattern. Accordingly, it may be sure that the nanophosphors of Examples 1 to 7 have been well formed in the range of extremely small particle size.

4. Observation of Chromaticity Diagram

Figure 4:
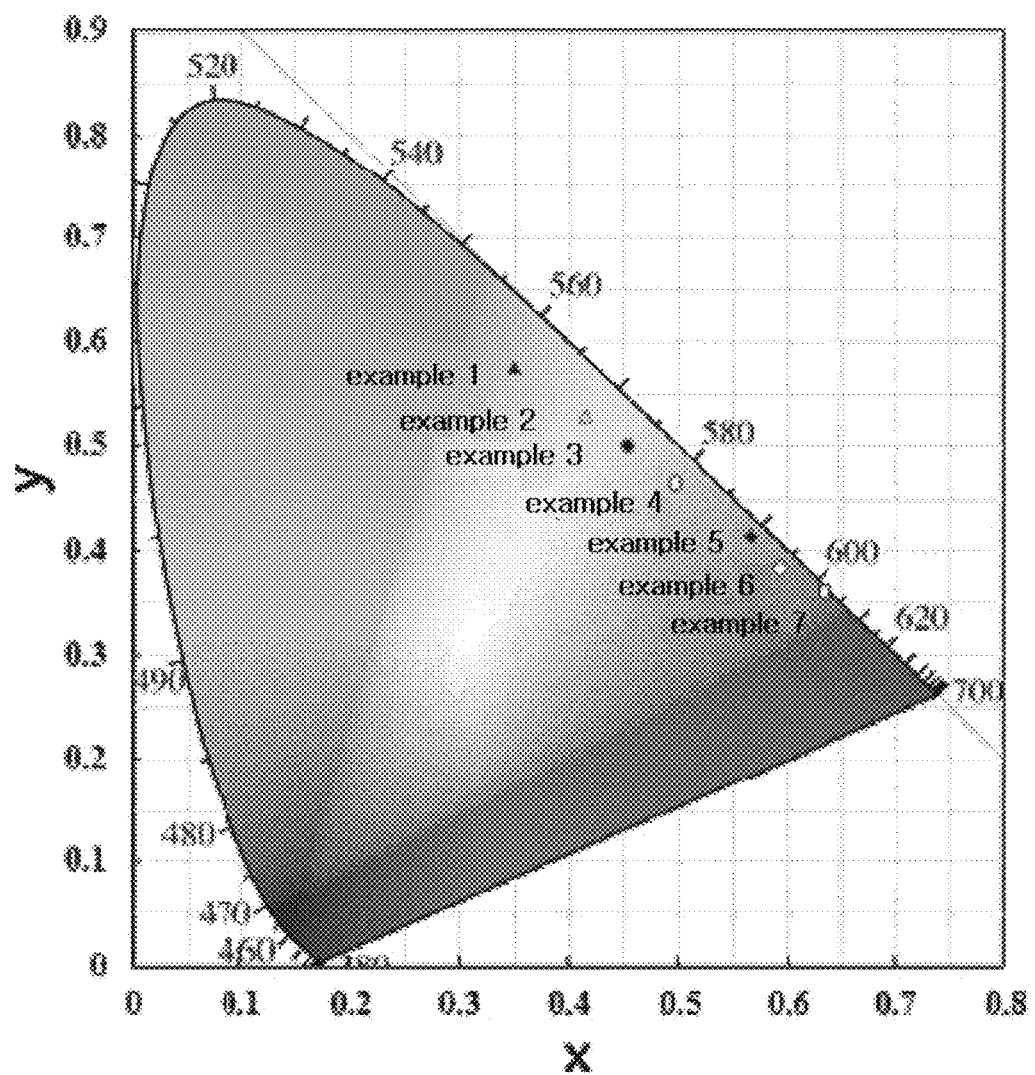

A CIE chromaticity diagram of the nanophosphors of Examples 1 to 7 are shown in FIG. 4. Referring to FIG. 4, as the same as being observed in FIG. 1, it can be noticed that the relative intensities of PL spectra of the green and red regions are changed in response to the variation of the contents of terbium and europium within the nanophosphor host, and accordingly the color emitted from each nanophosphor is tunable.

5. Observation by the Naked Eye under Ultraviolet Excitation Condition

Figure 5:
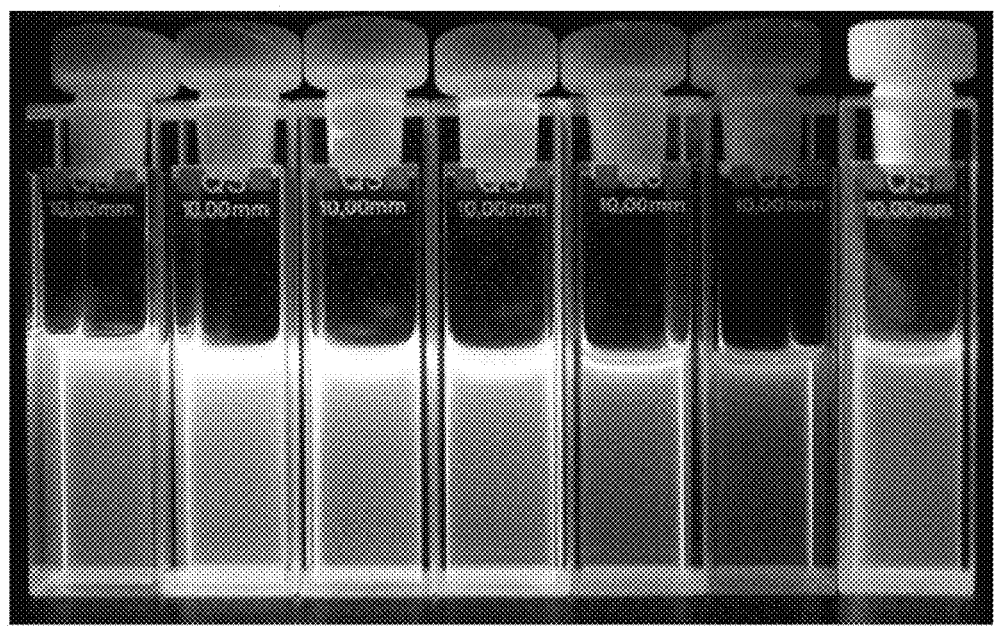

Photoluminescence images of the nanophosphors synthesized in Examples 1 to 7 are shown in FIG. 5. Referring to FIG. 5, it can be observed that the nanophosphors fabricated according to the present disclosure can emit various luminescent colors of green, yellowish green, yellow, orange and red under an excitation condition of the same wavelength of ultraviolet rays.

Example 8: Fabrication of Orange-Emitting Nanophosphor as 0.1 mmol $Ce^{3+}$, 0.15 mmol $Tb^{3+}$, 0.05 mmol $Eu^{3+}$-Doped Fluoride-Based Nanoparticle with Size Below 10 nm 0.05 mmol of yttrium chloride hydrate ($YCl_3.6H_2O$), 0.6 mmol of gadolinium chloride hydrate ($GdCl_3.6H_2O$), 0.1 mmol of cerium chloride hydrate ($CeCl_3.7H_2O$), 0.15 mmol of terbium chloride hydrate ($TbCl_3.6H_2O$), 0.05 mmol of europium chloride hydrate ($EuCl_3.6H_2O$), and 3.1 mmol of sodium oleate ($C_{18}H_{33}NaO_2$) were weighed, respectively, to be added into a mixture solvent (a mixture of water, ethanol, and hexane), thereby preparing a mixture. The mixture was heat treated at 70° C. to prepare a lanthanide complex compound (Complex compound preparing step).

The lanthanide complex compound was mixed with a solution containing oleic acid and 1-octadicene, and heat treated at 150° C. for 30 minutes, preparing a first mixed-solution containing the lanthanide complex compound (First mixed-solution preparing step).

2.5 mmol of sodium hydroxide was mixed with 10 ml of methanol solution containing 4 mmol of ammonium fluoride, to prepare a second mixed-solution. The second mixed-solution was then mixed with the first mixed-solution, to prepare a reaction-solution (Reaction-solution preparing step).

After fully mixing the reaction-solution, the methanol was removed, followed by heat treatment under an inert gas atmosphere. The heat treatment was carried out at 300° C. for 1.5 hours (Nanoparticle preparing step).

After completion of the heat treatment of the nanoparticle preparing step, the reaction-solution was cooled down to room temperature, thereby obtaining a nanophosphor in a colloid state having a diameter of about 4.9 nm. The thusly obtained nanophosphor was washed with acetone or ethanol, and stored by being dispersed in a non-polar solvent, such as hexane, toluene, chloroform and the like.

Example 9: Fabrication of Core-Shell Nanophosphor Having Fluoride-Based Nanoparticle β-$NaY_{0.1}Gd_{0.6}F_4:Ce^{3+}_{0.1},Tb^{3+}_{0.15}Eu_{0.05}$ nanoparticle having a size below 10 nm, obtained through Example 8, was used as a core, and a shell, which exhibited a magnetic characteristic, was formed around the core according to a method to be explained hereinafter.

A third mixed-solution was prepared by dissolving 1.0 mmol of gadolinium chloride hydrate ($GdCl_3.6H_2O$) in 6 ml of oleic acid and 15 ml of 1-octadicene. Afterwards, β-$NaY_{0.1}Gd_{0.6}F_4:Ce^{3+}_{0.1},Tb^{3+}_{0.15}Eu_{0.05}$ dispersed in 10 ml of hexane was added into the third mixed-solution, thereby preparing a fourth mixed-solution (Shell solution preparing step and nanoparticle mixing step).

After evenly mixing the fourth mixed-solution using a magnetic stirrer, 10 ml of methanol solution containing 2.5 mmol of sodium chloride and 4 mmol of ammonium chloride was injected into the fourth mixed-solution (Shell reaction-solution preparing step), followed by heat treatment as disclosed in Example 1 (Shell preparing step). After the heat treatment, the mixture was washed with ethanol, obtaining a nanophosphor having the core and the shell, with a size of about 8.8 nm. The nanophosphor of Example 9 was stored by being dispersed in chloroform.

Experimental Example: Evaluation of Characteristics of Nanophosphors of Examples 8 and 9

1. Observation of TEM Image

Figure 6:
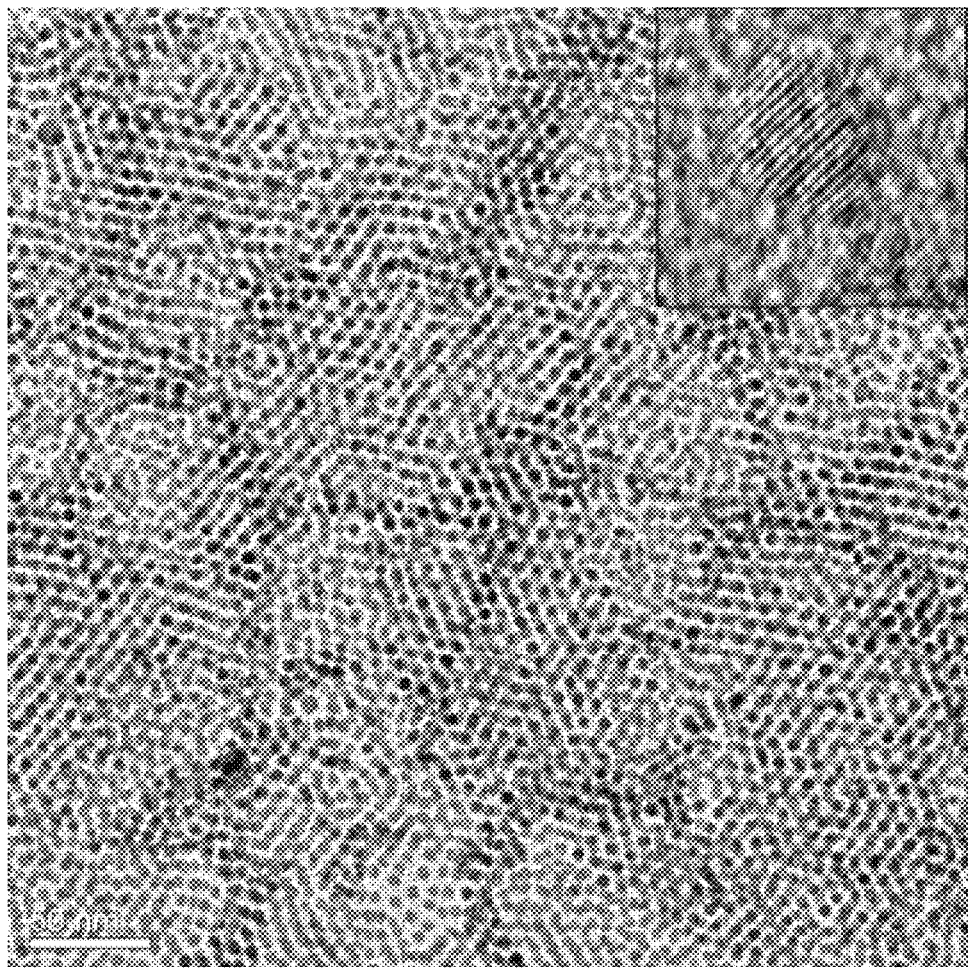
Figure 7:
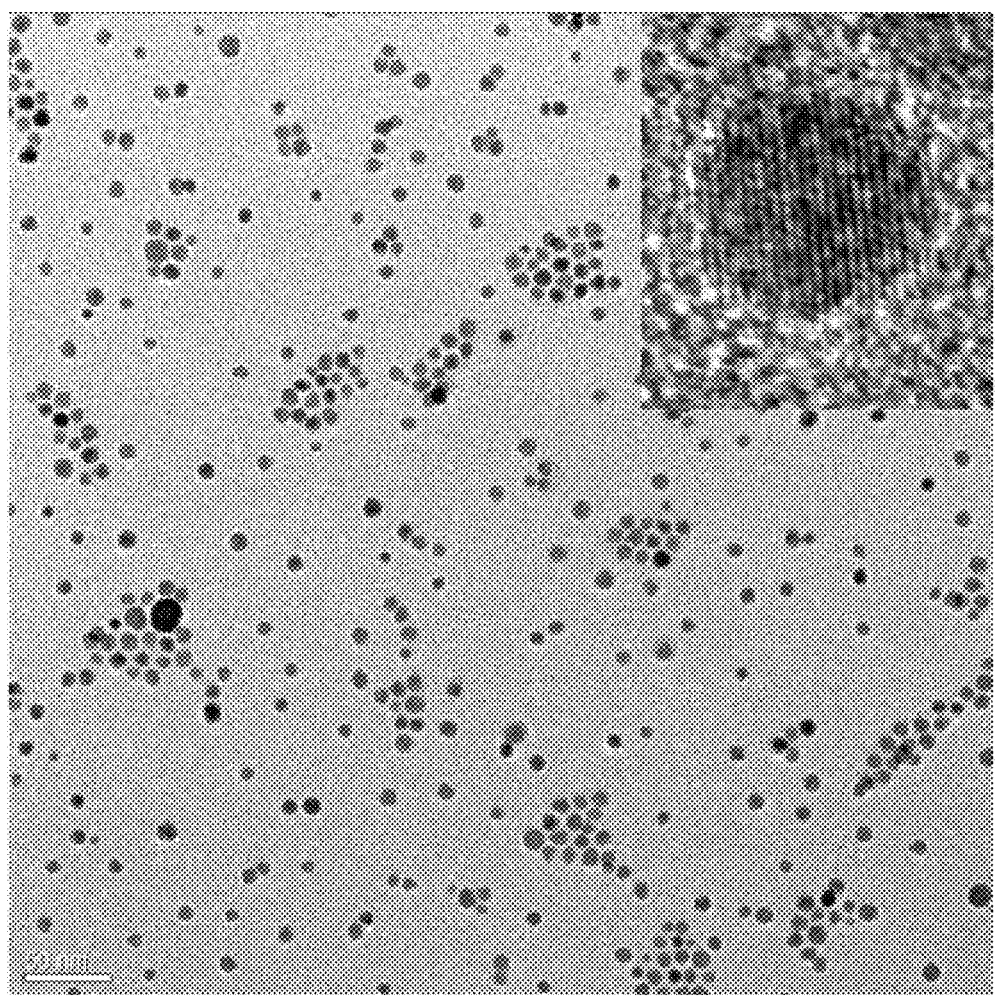

The nanophosphors of Examples 8 and 9 have been observed, respectively, using FEI TECNAI F20 G2, and the observed results are shown in FIGS. 6 and 7.

FIG. 6 is a TEM image and a high resolution TEM image of the nanophosphor synthesized in Example 8. Referring to FIG. 6, the nanophosphor synthesized in Example 8 has a size of 4.9 nm. Referring to the high resolution TEM image inserted in a right upper end of FIG. 6, a lattice pattern is clearly observed on one nanophosphor particle. This may indicate that the synthesized nanophosphor has an extremely high crystallinity. The nanophosphor of Example 8 may exhibit a strong PL characteristic by virtue of the high crystallinity in spite of the ultra small size below 10 nm.

FIG. 7 is a TEM image of a $\beta$-NaY$_{0.1}$Gd$_{0.6}$F$_4$:Ce$^{3+}$$_{0.1}$, Tb$^{3+}$$_{0.15}$Eu$_{0.05}$/$\beta$-NaGdF$_4$ core-shell nanophosphor, synthesized in Example 9. It can be observed that the core-shell nanophosphor synthesized in Example 9 has a size of 8.8 nm, which is greater than the nanophosphor of Example 8 used as the core, by virtue of the growth of the shell around the core. Referring to the high resolution TEM image shown on a right upper end of FIG. 7, it can be noticed that a lattice pattern of the core-shell nanoparticle is clearly observed and the shell has been epitaxially grown based on the continuous lattice pattern around the core nanoparticle.

2. Measurement of PL Spectrum

Photoluminescence spectra of the nanophosphor consisting of the nanoparticle synthesized in Example 8, and the core-shell nanophosphor synthesized in Example 9 have been measured using Hitachi F-7000, and the measurement results are shown in FIG. 8. Referring to FIG. 8, it can be observed that the photoluminescence of the nanophosphor of Example 9 has greatly increased as compared to Example 8. Also, compared to Example 8, the nanophosphor of Example 9 exhibits the increase in photoluminescence intensity by about 2.3 times than the nanophosphor of Example 8. This may result from the growth (formation) of the epitaxial shell around the core.

Example 10: Synthesis of Composite of Core-Shell Fluoride Nanophosphor and PDMS 0.4 ml of the core-shell nanophosphor obtained in Example 9 was mixed with 4 ml of polydimethylsiloxane (PDMS) and 0.4 ml of curing agent, preparing a core-shell nanophosphor polymer mixture. The mixture was cooled down to room temperature after being maintained at 80° C. for one hour, thereby obtaining nanophosphor-polymer composite of Example 10.

Experimental Example: Evaluation of Transparency and Photoluminescence Property The image of the nanophosphor-polymer composite of Example 10 is shown in FIG. 9.

Referring to a left image of FIG. 9, it can be noticed that the composite is very transparent and characters of a document laid under it are clearly visible. Also, referring to a right image of FIG. 9, which is a photoluminescence image obtained when the nanophosphor was excited by 254-nm ultraviolet lamp, a red luminescent color is observed. The synthesis of the nanophosphor-polymer composite having high transparency and superior photoluminescence property was confirmed from the images of FIG. 9.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A nanophosphor comprising a fluoride-based nanoparticle expressed by the following chemical formula 1 and co-doped with Ce$^{3+}$ and one selected from a group consisting of Tb$^{3+}$, Eu$^{3+}$ and a combination thereof,

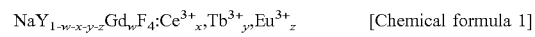
NaY$_{1-w-x-y-z}$Gd$_w$F$_4$:Ce$^{3+}$$_x$,Tb$^{3+}$$_y$,Eu$^{3+}$$_z$      [Chemical formula 1]

where x denotes a real number in the range of 0.1≤x≤0.5, y denotes a real number in the range of 0≤y≤0.4, z denotes a real number in the range of 0≤z≤0.3, w denotes a real number in the range of 0≤w≤0.9, and 0<y+z and 0≤w+x+y+z≤1 are satisfied.

2. A nanophosphor having a core-shell structure comprising:
a core comprising a fluoride-based nanoparticle expressed by chemical formula 1 and co-doped with Ce$^{3+}$ and one selected from a group consisting of Tb$^{3+}$, Eu$^{3+}$ and a combination thereof; and
a shell covering a surface of the core,
wherein the shell consists of a compound expressed by the following chemical formula 2,

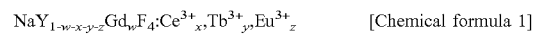
NaY$_{1-w-x-y-z}$Gd$_w$F$_4$:Ce$^{3+}$$_x$,Tb$^{3+}$$_y$,Eu$^{3+}$$_z$      [Chemical formula 1]

NaGd$_{1-r}$M$_r$F$_4$      [Chemical formula 2]

wherein in the chemical formula 1, x denotes a real number in the range of 0.1≤x≤0.5, y denotes a real number in the range of 0≤y≤0.4, z denotes a real number in the range of 0≤z≤0.3, w denotes a real number in the range of 0≤w≤0.9, and 0<y+z and 0≤w+x+y+z≤1 are satisfied, and
wherein in the chemical formula 2, r denotes a real number in the range of 0≤r<1, and M denotes one selected from a group consisting of yttrium (Y), lanthanide element and a combination thereof.

3. The nanophosphor of claim 1, wherein a size of the fluoride-based nanoparticle is in the range of 1 to 50 nm.

4. The nanophosphor of claim 1, wherein the fluoride-based nanoparticle has a hexagonal structure.

5. The nanophosphor of claim 2, wherein the nanophosphor having the core-shell structure is greater than 1 nm and 60 nm or less.

6. The nanophosphor of claim 1, wherein the nanophosphor has a down-conversion photoluminescence property of emitting a green, yellowish green, yellow, orange or red color under a single wavelength excitation according to the content of lanthanide elements.

7. The nanophosphor of claim 1, wherein the nanophosphor comprises a fluoride-based nanoparticle containing Tb$^{3+}$ and Eu$^{3+}$ in a molar ratio of 30 to 15:1, and has a yellowish green-emitting photoluminescence property.

8. The nanophosphor of claim 1, wherein the nanophosphor comprises a fluoride-based nanoparticle containing Tb$^{3+}$ and Eu$^{3+}$ in a molar ratio of 7 to 8:1, and has a yellow-emitting photoluminescence property.

9. The nanophosphor of claim 1, wherein the nanophosphor comprises a fluoride-based nanoparticle containing $Tb^{3+}$ and $Eu^{3+}$ in a molar ratio of 3 to 4:1, and has an orange-emitting photoluminescence property.

10. The nanophosphor of claim 1, wherein the nanophosphor comprises a fluoride-based nanoparticle containing $Tb^{3+}$ and $Eu^{3+}$ in a molar ratio of 1 to 2:1, and has a scarlet-emitting photoluminescence property.

11. A method of synthesizing a nanophosphor comprising:
a complex compound preparing step of heat treating a mixture including at least one selected from a group consisting of terbium precursor and europium precursor, yttrium precursor, gadolinium precursor, cerium precursor, oleic acid, and a mixture solvent to prepare a lanthanide complex compound;
a first mixed-solution preparing step of mixing the lanthanide complex compound with a solution including oleic acid and 1-octadecene to prepare a first mixed-solution containing the lanthanide complex compound;
a reaction-solution preparing step of mixing the first mixed-solution with a second mixed-solution including sodium precursor, fluorine precursor and alcohol to prepare a reaction-solution; and
a nanoparticle preparing step of forming a fluoride-based nanoparticle by removing the alcohol from the reaction-solution, followed by heat treatment,
wherein the nanoparticle is a fluoride-based nanoparticle expressed by chemical formula 1, and co-doped with $Ce^{3+}$ and one selected from a group consisting of $Tb^{3+}$, $Eu^{3+}$ and a combination thereof, $$NaY_{1-w-x-y-z}Gd_wF_4:Ce^{3+}{}_x,Tb^{3+}{}_y,Eu^{3+}{}_z \quad \text{[Chemical formula 1]}$$

where x denotes a real number in the range of $0.1 \leq x \leq 0.5$, y denotes a real number in the range of $0 \leq y \leq 0.4$, z denotes a real number in the range of $0 \leq z \leq 0.3$, w denotes a real number in the range of $0 \leq w \leq 0.9$, and $0 < y+z$ and $0 \leq w+x+y+z \leq 1$ are satisfied.

12. The method of claim 11, wherein the yttrium precursor is one selected from a group consisting of yttrium acetate $(Y(CH_3COO)_3)$, yttrium chloride $(YCl_3)$, yttrium chloride hydrate $(YCl_3.6H_2O)$, and any combination thereof,
wherein the gadolinium precursor is one selected from a group consisting of gadolinium acetate $(Gd(CH_3COO)_3)$, gadolinium chloride $(GdCl_3)$, gadolinium chloride hydrate $(GdCl_3.6H_2O)$, and any combination thereof,
wherein the cerium precursor is one selected from a group consisting of cerium acetate $(Ce(CH_3COO)_3)$, cerium chloride $(CeCl_3)$, cerium chloride hydrate $(CeCl_3.7H_2O)$, and any combination thereof,
wherein the terbium precursor is one selected from a group consisting of terbium acetate $(Tb(CH_3COO)_3)$, terbium chloride $(TbCl_3)$, terbium chloride hydrate $(TbCl_3.6H_2O)$, and any combination thereof, and
wherein the europium precursor is one selected from a group consisting of europium acetate $(Eu(CH_3COO)_3)$, europium chloride $(EuCl_3)$, europium chloride hydrate $(EuCl_3.6H_2O)$, and any combination thereof.

13. The method of claim 11, wherein the heat treatment in the nanoparticle preparing step is carried out at temperature of 200 to 370° C. for 10 minutes to four hours.

14. The method of claim 11, further comprising a shell preparing step after the nanoparticle preparing step,
wherein the shell preparing step comprises:
a shell solution preparing step of preparing a third mixed-solution containing lanthanide precursor comprising gadolinium precursor, oleic acid, and 1-octadecene;
a nanoparticle mixing step of heat treating the third mixed-solution to form gadolinium oleate therein and mixing the heat treated third mixed-solution with fluoride-based nanoparticles to prepare a fourth mixed-solution;
a shell reaction-solution preparing step of to mix the fourth mixed-solution with a solution containing sodium precursor, fluorine precursor and alcohol to prepare a shell reaction-solution; and
a shell forming step of growing a shell on a surface of a core, which comprises the fluoride-based nanoparticles, by removing the alcohol from the shell reaction-solution, followed by heat treatment, and
wherein the shell consists of a compound expressed by the following chemical formula 2, $$NaGd_{1-r}M_rF_4 \quad \text{[Chemical formula 2]}$$

where r denotes a real number in the range of $0 \leq r < 1$, and M denotes one selected from a group consisting of yttrium (Y), lanthanide element and a combination thereof.

15. The method of claim 14, wherein the gadolinium precursor is one selected from a group consisting of gadolinium acetate $(Gd(CH_3COO)_3)$, gadolinium chloride $(GdCl_3)$, gadolinium chloride hydrate $(GdCl_3.6H_2O)$, and any combination thereof.

16. A nanophosphor-polymer composite comprising the nanophosphor according to claim 1 and a polymer.

17. A nanophosphor-polymer composite comprising the nanophosphor according to claim 2 and a polymer.

18. A fluorescent or magnetic resonance imaging contrast agent comprising the nanophosphor according to claim 1.

19. An anti-counterfeit code comprising the nanophosphor according to claim 1.

* * * * *